US010689978B2

(12) United States Patent
Al-Sofi et al.

(10) Patent No.: US 10,689,978 B2
(45) Date of Patent: Jun. 23, 2020

(54) METHOD FOR DETERMINING GELATION TIME IN A CORE PLUG

(71) Applicant: Saudi Arabian Oil Company, Dhahran (SA)

(72) Inventors: Abdulkareem M. Al-Sofi, Dhahran (SA); Jinxun Wang, Dhahran (SA); Hassan Wasel Al Hashim, Ad Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 203 days.

(21) Appl. No.: 15/994,272

(22) Filed: May 31, 2018

(65) Prior Publication Data

US 2019/0368349 A1    Dec. 5, 2019

(51) Int. Cl.
*G01N 15/08* (2006.01)
*E21B 49/02* (2006.01)
(Continued)

(52) U.S. Cl.
CPC ............ *E21B 49/02* (2013.01); *E21B 49/005* (2013.01); *G01N 15/0826* (2013.01); *G01N 11/00* (2013.01)

(58) Field of Classification Search
CPC .. G01N 15/08; G01N 15/082; G01N 15/0826; G01N 2291/02441;
(Continued)

(56) References Cited

U.S. PATENT DOCUMENTS 3,785,437 A * 1/1974 Clampitt .................. C09K 8/42
166/281
4,691,558 A * 9/1987 Vinson .................... G01N 11/00
73/64.41
(Continued)

FOREIGN PATENT DOCUMENTS

EP    0188856 A1    1/1985
GB    2145420 A    3/1985
(Continued)

OTHER PUBLICATIONS

Bertin et al., "Foam Flow in Heterogeneous Porous Media: Effect of Crossflow", SPE/DOE Improved Oil Recovery Symposium, Apr. 19-22, 1998.
(Continued)

*Primary Examiner* — Alexander A Mercado
(74) *Attorney, Agent, or Firm* — Dinsmore & Shohl

(57) ABSTRACT

A method of determining gelation time is disclosed that includes placing a composite core plug into a core holder of a commercially-available vessel. The composite core plug includes a first core plug with second and third core plugs disposed on opposite sides of the first core plug. The second and third core plugs are saturated with polymer solution, and the first core plug is saturated with gel solution comprising polymer and crosslinker. The method further includes alternating polymer solution injections between a first injection area located on the second core plug and a second injection area located on the third core plug, while ensuring that the polymer solution is being continuously fed to the composite core plug. The pressure drop across the composite core plug is monitored during the alternating injection of polymer solution to determine the gelation time of the gel solution in the first core plug.

20 Claims, 2 Drawing Sheets

(51) Int. Cl.
*E21B 49/00* (2006.01)
*G01N 11/00* (2006.01)

(58) Field of Classification Search
CPC . G01N 2291/0251; G01N 2291/02872; G01N 11/00; G01N 11/02; G01N 2011/0026; G01F 22/00; G01L 13/00; G01L 15/00
USPC .................................................. 73/64.41
See application file for complete search history.

(56) References Cited

U.S. PATENT DOCUMENTS

| | | | |
|---|---|---|---|
| 4,941,533 A * | 7/1990 | Buller | C09K 8/594 166/246 |
| 5,042,296 A * | 8/1991 | Burgess | E21B 21/08 73/152.19 |
| 5,247,828 A * | 9/1993 | Candau | G01N 29/02 73/64.42 |
| 5,261,267 A | 11/1993 | Kamath et al. | |
| 5,992,223 A * | 11/1999 | Sabins | G01N 29/032 73/54.03 |
| 7,805,982 B2 | 10/2010 | Hilab | |
| 7,861,609 B2 | 1/2011 | Haggerty et al. | |
| 2006/0278390 A1 | 12/2006 | Reddy et al. | |
| 2018/0335374 A1* | 11/2018 | Kanj | G01N 15/0826 |
| 2019/0391065 A1* | 12/2019 | Karazincir | G01N 33/24 |

FOREIGN PATENT DOCUMENTS

| | | |
|---|---|---|
| WO | 8600330 A1 | 1/1986 |
| WO | 2011098770 A1 | 8/2011 |

OTHER PUBLICATIONS

He et al., "Comparison of Gelation Behavior and Morphology of Resorcinol-Hexamethylenetetramine-HPAM Gel in Bulk and Porous Media", Transp Porous Med, vol. 109, pp. 377-392, 2015.

Huang et al., "An Experimental Study of the In-Situ Gelation of Chromium(+3)/Polyacrylamide Polymer in Porous Media", SPE Reservoir Engineering, pp. 583-592, Nov. 1986.

Hubbard et al., "Experimental and Theoretical Investigation of Time-Setting Polymer Gels in Porous Media", SPE Reservoir Engineering, pp. 1257-1267, Nov. 1986.

Sengupta et al., "In-situ Gelation Studies of an Eco-friendly Cross-linked Polymer System for Water Shut-off at High Temperatures", Energy Sources, Part A, vol. 36, pp. 1445-1467, 2014.

Vasquez et al., "Laboratory Evaluation of High-Temperature Conformance Polymer Systems", SPE Production and Operations Symposium, Mar. 23-26, 2003.

Vasquez et al., "Development and Evaluation of High-Temperature Conformance Polymer Systems", SPE International Symposium on Oilfield Chemistry, Feb. 2-4, 2005.

Wang et al., "Development and Evaluation of Gel-based Conformance Control for a High Salinity and High Temperature Carbonate", SPE EOR Conference at Oil and Gas West Asia, Mar. 21-23, 2016.

Zhuang et al., "A Novel EOR Polymer (II)—Investigation on In-Situ Gelation on SMRF System in Berea Core", Chinese Journal of Polymer Science, vol. 13, No. 1, pp. 66-73, Mar. 20, 1995.

International Search Report and Written Opinion dated Mar. 7, 2019 pertaining to International application No. PCT/US2018/041359 filed Jul. 10, 2018, 14 pgs.

* cited by examiner

METHOD FOR DETERMINING GELATION TIME IN A CORE PLUG

TECHNICAL FIELD

The present disclosure relates to determining gelation time of a core plug of a geologic formation, usually reservoir rock, taken during or after drilling a well.

BACKGROUND

Economic and efficient oil and gas production is dependent on understanding key properties of reservoir rock and fluid, such as porosity, permeability, compressibility, wettability, formation flow potential, fracture orientation, and fluid compatibility. Geoscientists have developed a variety of approaches, including log and core analysis techniques, to measure these properties. Core analysis is especially important in geologic formations with vertical and lateral heterogeneity. Core analysis can include evaluation of rock properties and anisotropy; organic matter content, maturity, and type; fluid content; fluid sensitivity; and geomechanical properties. This information can be used to calibrate log and seismic measurements and to help in well and completion design, well placement, and other aspects of reservoir production.

SUMMARY

Conventional methods for determining gelation time cannot give an accurate measurement of gelation time in situ. For example, the conventional bottle test for gelation time is often conducted at ambient pressure, and is more prone to evaporation during testing. In order to determine in situ gelation time, large core plugs are needed and specialized coreholding setups, which must be used, are not commercially-available. Conventional coreholding setups cannot be used due to the large size of the core plugs. Therefore, a need exists for a method for accurately determining gelation time in a core plug at in situ conditions utilizing commercially-available coreholders.

In accordance with one embodiment of the present disclosure, a method of determining gelation time is disclosed. The method includes placing a composite core plug into a core holder of a vessel. The vessel may be a commercially-available coreholder, and each core plug is cylindrical. The composite core plug includes a first core plug with second and third core plugs disposed on opposite sides of the first core plug. Specifically, the second and third core plugs may each couple to each respective end of the first core plug. The flat surfaces of the first core plug and the second core plug may be coupled together on one end of the first core plug, and the flat surfaces of the first core plug and the second core plug may be coupled together on the opposite end of the first core plug. The second and third core plugs are saturated with polymer solution, and the first core plug is saturated with gel solution comprising polymer and crosslinker. The method further includes alternating polymer solution injections between a first injection area located on the second core plug and a second injection area located on the third core plug, while ensuring that the polymer solution is being continuously fed to the composite core plug. Lastly, the method includes monitoring the pressure drop, or pressure profile change, across the composite core plug during the alternating injection of polymer solution to determine the gelation time of the gel solution in the first core plug. A commercially-available coreholder may be used for this method as the composite core plug is a size that may be tested using a commercially-available coreholder.

Additional features and advantages of the described embodiments will be set forth in the detailed description which follows. The additional features and advantages of the described embodiments will be, in part, readily apparent to those skilled in the art from that description or recognized by practicing the described embodiments, including the detailed description which follows as well as the drawings and the claims.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
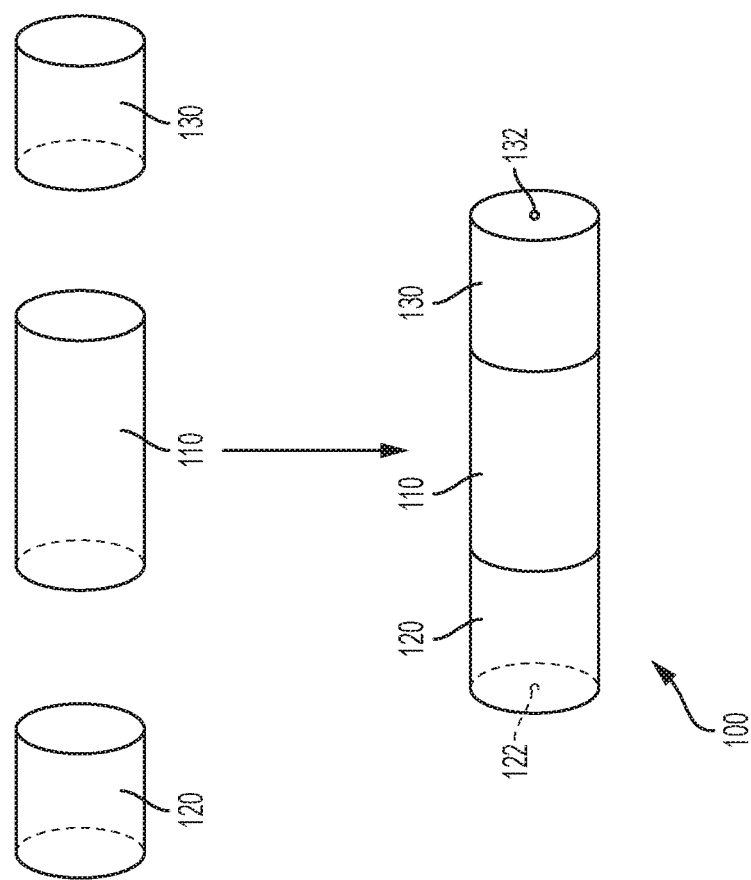
FIG. 1 illustrates three core plugs connected into one composite core plug, according to one or more embodiments described in this disclosure.

As used throughout this disclosure, the term "composite core plug" refers to a combined core plug including the first, second, and third core plugs.

As used throughout this disclosure, the term "coreflooding" refers to a test in which a fluid or combination of fluids is injected into a core plug. Objectives include measurement of permeability, relative permeability, saturation change, formation damage caused by the fluid injection, or interactions between the fluid and the rock, such as the gelation time of the fluid. The core material often comes from an oil reservoir, but some tests use outcrop rock. The fluid in place at the start of the test is typically either a simulated formation brine, oil, or a combination of brine and oil. Injected fluids may include crude oil, simulated reservoir brine, refined fluids, drilling mud filtrate, acids, foams, gel solutions, or other chemicals used in the oil field. Pressures and flow rates at both ends of the core are measured.

As used throughout this disclosure, the term "coreflooding coreholder" refers to a coreholder vessel equipped to conduct coreflooding experiments and measurements, including coreflooding gelation time testing.

As used throughout this disclosure, the term "coreholder" refers to a vessel designed to withstand elevated temperatures and pressures, such as up to 20,000 pounds per square inch (psi) (137,895 kilopascals (kPa); 1 psi=6.89476 kPa) and 300° C., and to test core plugs at these elevated temperatures and pressures.

As used throughout this disclosure, the term "core plug" refers to a plug, or sample, taken from a whole core from a formation for analysis. Core plugs are conventionally 1 to 1.5 in. (2.5 to 3.8 centimeters (cm); 1 in.=2.54 cm) in diameter and 1 to 2 inches (in.) (5 cm) long. Core plugs are conventionally cut perpendicular to the axis of the core or parallel to the axis, which form horizontal and vertical plugs, respectively, when cut from a vertical wellbore. Conventional core plug analysis is conducted in a coreholder.

As used throughout this disclosure, the term "formation" refers to a body of rock that is sufficiently distinctive and continuous from the surrounding rock bodies that the body of rock can be mapped as a distinct entity. A formation is, therefore, sufficiently homogenous to form a single identifiable unit containing similar rheological properties throughout the formation, including, but not limited to, porosity and permeability. A formation is the fundamental unit of lithostratigraphy.

As used throughout this disclosure, the term "pore volume" refers to the ratio of a porous material's air volume to a porous material's total volume.

As used throughout this disclosure, the term "reservoir" refers to a subsurface formation having sufficient porosity and permeability to store and transmit fluids.

As used throughout this disclosure, the term "saturated" refers to the almost complete filling (such as 0.6 pore volume (PV), 0.8 PV, 0.9 PV, 0.95 PV, or 0.99 PV or above) of the core sample pore volume with a given fluid.

As used throughout this disclosure, the term "viscous fingering" refers to a phenomena whereby the interface of two fluids, in which one fluid has a lesser viscosity than the other, such as a difference of more than 5 centiPoise (cP), 10 cP, 20 cP, or 50 cP, and bypasses sections of the porous media as it moves along, creating an uneven, or fingered, profile. Fingering is a relatively common condition when injecting solutions with a viscosity of less than 10 cP into porous media.

As used throughout this disclosure, the term "whole core" refers to a complete section of a conventionally-drilled core. The section may be up to approximately 2 feet ((60 cm); 1 foot=30.48 cm) in length, with conventional core diameters lying between 1.75 and 5.25 in. (4.4 and 13.3 cm).

The present disclosure is directed to methods for determining gelation time in core plugs at in situ conditions. Gelation time is the time when a gel solution starts to form gel. It is an important parameter for screening gel formulations, characterizing gel formulation performance, and designing gel treatments. The method includes placing a composite core plug into a core holder of a vessel. The vessel may be a commercially-available coreholder, and each core plug is cylindrical. The composite core plug includes a first core plug with second and third core plugs disposed on opposite sides of the first core plug. Specifically, the second and third core plugs may each couple to each respective end of the first core plug. The flat surfaces of the first core plug and the second core plug may be coupled together on one end of the first core plug, and the flat surfaces of the first core plug and the second core plug may be coupled together on the opposite end of the first core plug. The second and third core plugs are saturated with polymer solution, and the first core plug is saturated with gel solution comprising polymer and crosslinker. The method further includes alternating polymer solution injections between a first injection area located on the second core plug and a second injection area located on the third core plug, while ensuring that the polymer solution is being continuously fed to the composite core plug. The injection area may include a point on, a part of, or the entirety of the exposed end, face, or surface of the second or third core plug. The polymer solution may be injected in an injection point or may be injected along the entire exposed face of the second or third core plug. Lastly, the method includes monitoring the pressure drop, or pressure profile change, across the composite core plug during the alternating injection of polymer solution to determine the gelation time of the gel solution in the first core plug. The gelation time is determined through monitoring the pressure response while the gel solution resides in the first core plug. In-situ gelation times can be determined using normal length core or core composite, with conventional coreholders, and without the need for multiple pressure taps.

Referring now to FIG. 1, an example composite core plug 100 is illustrated. The first core plug 110 is composite with the second core plug 120 and the third core plug 130 to form the composite core plug 100. The diameter, porosity, and permeability of the second core plug 120 may be within 0.1%, 0.5%, 1%, 2%, or 5% of a diameter, porosity, and permeability of the third core plug 130. The second core plug 120 and the third core plug 130 may be cut from the same whole core. The first core plug 110 may be saturated with the gel solution and the second core plug 120 and the third core plug 130 may be saturated with the polymer solution prior to combining the three core plugs to form the composite core plug 100.

To determine gelation time in the core plugs at in situ conditions, the method may be conducted at in situ confining pressure and temperature. Confining pressure, or geostatic pressure, is the pressure of the weight of overburden, or overlying rock, on a formation. The confining pressure and temperature will vary depending on the depth, type of formation, and reservoir conditions meant to be simulated. The confining pressure may be from 200 to 3000 psi (1378.95 to 20684.27 kPa), from 300 to 2500 psi (2068.43 to 17236.89 kPa), from 500 to 2000 psi (3447.38 to 13789.51 kPa), or from 800 to 1500 psi (5515.81 to 10342.14 kPa). The temperature may be from 50 to 150° C., from 80 to 125° C., from 90 to 115° C., or from 95 to 110° C. The method may further be conducted with a specific backpressure. Backpressure is the pressure opposed to the desired flow of liquids registered on testing equipment. The backpressure may be from 25 to 450 psi (172.36 to 3102.64 kPa), from 50 to 350 psi (344.738 to 2413.17 kPa), from 80 to 300 psi (551.58 to 2068.43 kPa), or from 100 to 250 psi (689.476 to 1723.69 kPa).

The polymer solution is used, rather than a solution with a viscosity of less than 50 cP, less than 20 cP, less than 15 cP, less than 10 cP, less than 8 cP, less than 5 cP, or less than 2 cP, to saturate the second and third core plugs to minimize the dilution of the polymer concentration in the gel solution due to mixing. A solution with a viscosity of less than 50 cP, less than 20 cP, less than 15 cP, less than 10 cP, less than 8 cP, less than 5 cP, or less than 2 cP may be an aqueous solution. The polymer solution may have a viscosity of greater than 50 cP, greater than 20 cP, greater than 15 cP, greater than 10 cP, greater than 8 cP, greater than 5 cP, or greater than 2 cP. Additionally, saturating the second and third core plugs with polymer solution, instead of a solution with a viscosity of less than 10 cP, minimizes viscous fingering and dispersion of the polymer solution into the gel solution during subsequent injection, due to the similar viscosities of the polymer solution and the gel solution. The polymer solution is used as the injection fluid for the same rationale due to the similar viscosities of the polymer solution and the gel solution. The polymer solution may have a viscosity within 1%, 3%, 5%, 10%, 20%, or 50% of a viscosity of the gel solution before gelation. The polymer solution is injected into the composite core plug where pressures are monitored to observe gelation time with conventional coreholders, and without the need for pressure taps. The pressures are monitored downstream of the injection areas, or upstream of the injection areas, or at a location proximate to the injection areas.

Various polymer solution components are contemplated and may include polyacrylamide, polyvinyl alcohol, polyacrylic acid, polyacrylonitrile, acrylamide copolymers, biopolymers, polysaccharides, or xanthan gum, for example. Biopolymers are polymeric biomolecules, or polymers produced by living organisms. The three main classes of biopolymers are polynucleotides, polypeptides, and polysaccharides. Polysaccharides are often linear bonded polymeric carbohydrate structures. Xanthan gum is a polysacchararide that may be used as a thickening agent and stabilizer. Other possible polysacchararides include, but are not limited to, schizophyllan and scleroglucan. The polymer solution may include total dissolved solids of from 35,000 to 80,000 milligrams per liter (mg/L) (35,000 to 80,000 kilograms per cubic meter ($kg/m^3$); 1 mg/L=1 $kg/m^3$), from 15,000 to 120,000 mg/L (15,000 to 120,000 $kg/m^3$), or from 5,000 to 200,000 mg/L (5,000 to 200,000 $kg/m^3$). The polymer solution may include a weight averaged molecular weight of from 10 million to 30 million Daltons, 15 million to 25 million Daltons, or 15 million to 20 million Daltons. The polymer solution may have a hydrolysis degree of from 20% to 40%, of from 25% to 35%, or of 30%.

As previously discussed in this disclosure, the gel solution includes polymer and crosslinker, whereas the polymer solution includes polymer without crosslinker. The crosslinker may be at least one of hexamethylenetetramine, resorcinol, chromium acetate, chromium malonate, and polyethyleneimine. The gel solution may include the same polymer used in the polymer solution. In some embodiments, the gel solution includes at least one of polymer, hexamethylenetetramine, and resorcinol.

The method may further include saturating the first, second, and third core plugs with an aqueous solution prior to saturating the first core plug with the gel solution and the second and third core plugs with polymer solution. Saturating the first core plug with the gel solution and the second and third core plugs with polymer solution displaces the aqueous solution in the core plugs.

In some embodiments, the aqueous solution may include one or more than one of fresh water, salt water, brine, connate brine, municipal water, formation water, produced water, well water, filtered water, distilled water, and sea water. In some embodiments, the aqueous solution may include water or a solution containing water and one or more inorganic compounds dissolved in the water or otherwise completely miscible with the water. In some embodiments, the aqueous solution may contain brine, including natural and synthetic brine. Brine includes water and a salt that may include calcium chloride, calcium bromide, sodium chloride, sodium bromide, other salts, and combinations of these. The aqueous solution may include total dissolved solids of from 150,000 to 300,000 mg/L (150 to 300 $kg/m^3$).

Referring again to FIG. 1, as previously discussed in this disclosure, the method further includes alternating polymer solution injections between a first injection area 122 located on the second core plug 120 and a second injection area 132 located on the third core plug 130, while ensuring that the polymer solution is being continuously fed to the composite core plug 100. The polymer solution may be injected in an injection point or may be injected along the entire exposed face, or surface, of the second or third core plug. Each alternating polymer solution injection may include injecting up to 0.5 PV, up to 0.4 PV, up to 0.25 PV, up to 0.2 PV, up to 0.15 PV, up to 0.1 PV, up to 0.08 PV, or up to 0.05 PV of the first core plug per injection. The volume of each alternating polymer solution injection, alternatively, may be governed by the second and third core plugs pore-volumes such that dilution and production of the gelant mixture is eliminated or at least minimized. Specifically, to ensure the fluid in the middle core is not produced, the maximum permissible pore volume to be injected may be the pore volume of the opposing end plug. For example, the pore volume injected into the second core plug may be governed by the pore volume of the third core plug, and vice versa. Without being limited by theory, this pore volume may be approximately equivalent to 0.5 PV of the first core plug. To avoid fluid breakthrough, such as fluid production from the first core plug, no more than 0.5 PV, 0.4 PV, 0.3 PV, 0.25 PV, 0.2 PV, 0.15 PV, 0.1 PV, 0.08 PV, or 0.05 PV of the first core plug may be injected. This value may alternatively be expressed as no more than 1 PV, 0.8 PV, 0.6 PV, 0.5 PV, 0.4 PV, 0.3 PV, 0.2 PV, 0.16 PV, or 0.1 PV of the second or third core plug.

In another embodiment, each alternating polymer solution injection may include injecting equal amounts of polymer solution in each injection. It is contemplated that alternating polymer solution injections further includes injecting the polymer solution at a constant flow rate, which may be from 0.05 to 0.2 milliliter per minute (ml/min) (0.00083 to 0.0033 cubic centimeters per second (cc/s); 1 ml/min=0.0167 cc/s), from 0.8 to 0.15 ml/min (0.0013 to 0.0025 cc/s), or 0.1 ml/min (0.00167 cc/s).

Alternating the polymer solution injections while ensuring the polymer solution is being continuously fed to the composite core plug allows for continuous, but alternating, flow of the gel solution within the composite core plug. Alternating the polymer solution injection area ensures that the gel solution remains within the first core plug of the composite core plug, so that the measured gelation time is an accurate gelation time for the gel solution in the porous media of the first core plug. By continuously injecting the polymer solution, the testing method more accurately simulates in situ gel solution injection conditions. When a gel solution is injected downhole into a formation, the gel solution is being continuously pumped into the formation, meaning that the gel solution is in a state of constant flow. Therefore, continuously injecting the polymer solution into the composite core plug more accurately simulates in situ gel formation, resulting in a more accurate measurement of gelation time.

Injecting the polymer solution, as opposed to a solution with a viscosity of less than 10 cP, reduces the viscous fingering phenomena in the composite core plug because the polymer solution and the gel solution have similar viscosities. When the viscosity of a displacing fluid is lesser than that of displaced fluid, the displacing fluid will exhibit less resistance and a tendency to advance faster. This contrast in viscosity yields viscous fingering, where instabilities arise in the form of the less viscous displacing fluid fingering through the more viscous displaced fluid. Therefore, if an solution with a viscosity less than 10 cP is injected, it will finger through the polymer solution and have a tendency of breaking into the gel solution in the first core plug and diluting the gel solution, which will yield an inaccurate gelation time. It is not viable to inject the gel solution because gel would form at the injection areas, or outside the core plug, and block the inlet and outlet injection tubing of the coreflooding coreholder. Using the polymer solution as the injection solution prevents gel from forming at the injection areas and yields a more uniform displacement which prevents viscous fingering and yields a more accurate gelation time.

Constant flow in a porous medium provides mixing and agitation to the gel solution. Agitating the gel solution, which includes the polymer and crosslinker, triggers crosslinking of the polymer chains, which causes the onset of gelation. The continuous flow of this method better replicates the in situ condition of pumping the gel solution into a formation by simulating constant flow, therefore more accurately measuring the gelation time and generating more representative data.

EXAMPLE

The following example illustrates features of the present disclosure but is not intended to limit the scope of the disclosure.

Example 1

Three core plugs from a carbonate reservoir were used for a gelation time test. The detailed properties of these three core plugs are presented in Table 1. The three-plug composite core plug is built as shown in FIG. 1, with first core plug 110 in the middle and second core plug 120 and third core plug 130 on either side of the first core plug 110. The second core plug 120 and the third core plug 130 were cut from the same core plug.

TABLE 1

Core plug properties.

| Core plug | Length, cm | Diameter, cm | Porosity, % | Permeability, md |
|---|---|---|---|---|
| First Core Plug | 4.329 | 3.772 | 23.7 | 706 |
| Second Core Plug | 2.009 | 3.780 | 25.6 | 551 |
| Third Core Plug | 1.758 | 3.780 | 25.6 | 551 |

A synthetic connate brine, with total dissolved solids (TDS) of 229,870 mg/L, was prepared for saturating core plug samples. A synthetic sea water with 57,670 mg/L TDS was used to prepare polymer solutions. Detailed brine compositions are presented in Table 2.

TABLE 2

Synthetic brine and water compositions.

| | $Na^+$, mg/L | $Ca^{2+}$, mg/L | $Mg^{2+}$, mg/L | $Cl^-$, mg/L | $HCO_3^-$, mg/L | $SO_4^{2-}$, mg/L | TDS, mg/L |
|---|---|---|---|---|---|---|---|
| Connate brine | 66,052 | 19,008 | 2,239 | 140,580 | 384 | 1,620 | 229,870 |
| Sea water | 18,300 | 650 | 2,110 | 32,200 | 120 | 4,290 | 57,670 |

An organically crosslinked polymer gel solution including 4,000 mg/L polymer, 1200 mg/L hexamethylenetetramine (HMTA), and 400 mg/L resorcinol, was used for the test. The polymer used for the test was a polyacrylamide (Flopaam™ 3630 S, produced by SNF Floerger) with a molecular weight of 20 million Dalton and 30% hydrolysis degree. The polymer solution including 4,000 mg/L polyacrylamide was prepared in synthetic sea water.

The clean and dry core plugs were first fully saturated with the synthetic connate brine under vacuum. Each plug was then individually loaded into a coreholder, and around 2.0 PV of the gel solution was injected into the first core plug 110 at room temperature, saturating the first core plug 110. Around 2.0 PV of the polymer solution was injected into the second core plug 120 and the third core plug 130 at room temperature, saturating the second core plug 120 and the third core plug 130. Following that, the composite core plug 100 was then built as shown in FIG. 1, with the gel saturated first core plug 110 between the second core plug 120 and the third core plug 130. The composite core plug 100 was then loaded into a coreflooding coreholder. A confining pressure of 1400 psi and a backpressure of 200 psi were then applied, the coreflooding coreholder system was heated to 95° C. before conducting the coreflooding gelation time test.

The coreflooding gelation time test was conducted by injecting the polymer solution at a constant flow rate of 0.1 ml/min. The injection was alternately injected from the first injection area 122 and the second injection area 132, and each injection amount was around 0.1 PV of the first core plug 110. The same amount of polymer solution was injected each alternation. The small injection amount maintains the gel solution flowing in the first core plug 110, and the same injection amount from both directions maintains the gel solution in the first core plug 110 after each injection cycle. An injection cycle is the completion of two total injections, one injection at the first injection area, and one injection at the second injection area.

Figure 2:
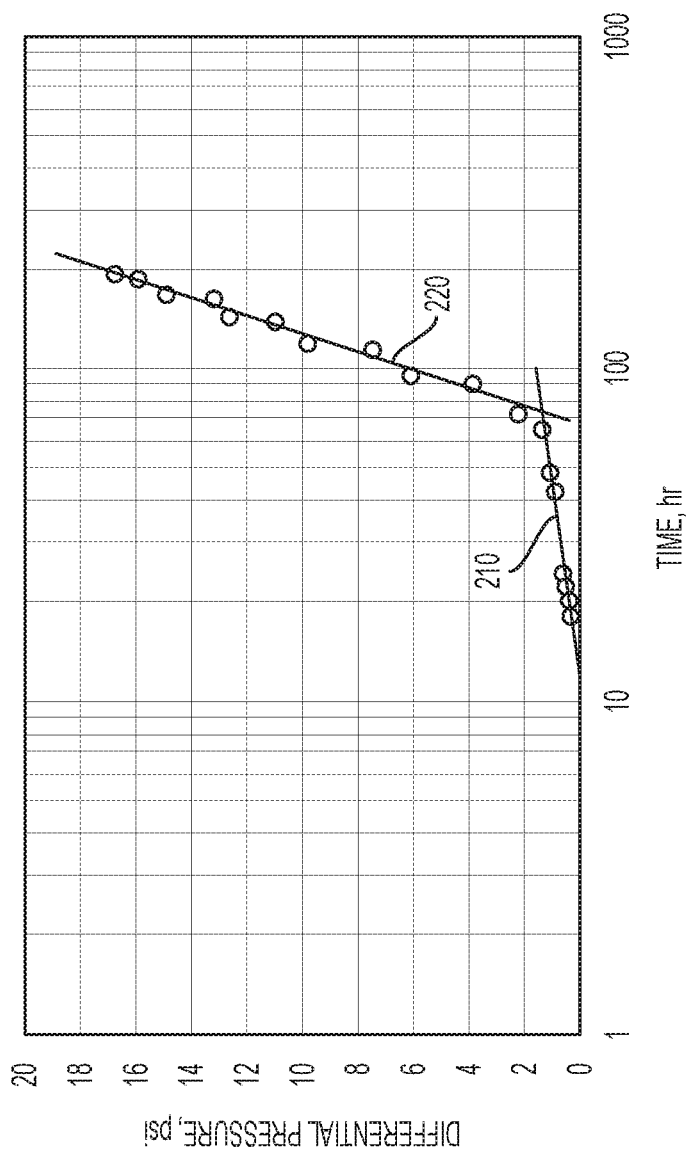
FIG. 2 graphically depicts the relationship between differential pressure (y-axis) and time (x-axis) during gelation time testing, according to one or more embodiments described in this disclosure.

The test was conducted and differential pressure response was recorded as a function of time. The recorded differential pressure as a function of time is presented in FIG. 2. Not intending to be bound by theory, it is believed that gelation time is determined as the time point at which the slope of the pressure differential changes from a first slope to a second slope, where the first slope is less than the second slope. This increase in flow resistance is due to the formation of gel. The first slope 210 represents a slow increase in differential pressure and the second slope 220 represents a rapid increase in differential pressure. The second slope 220 begins to form at approximately 74 hours, and therefore the gelation time is determined to be 74 hours. This measurement is a more accurate measurement of in situ gelation time than the 72 hour gelation time observed in a bottle test run for the same gel solution at 95° C. Bottle tests are often used to rapidly determine gelation time by periodically observing the flowability of the gel solution in the bottle. The flowability of the gel solution is observed by slightly tilting and inverting the bottle. In bottle testing, the gelation time is determined as the time point when an elastic tongue-shaped gelant partially flows out with a tongue of several centimeters long, when the bottle is uncapped and inverted. As such, this example method is more accurate than the bottle testing method because the example method was conducted at in situ simulated formation pressure and temperature, whereas the bottle testing method was only conducted at in situ simulated formation temperature. Without in situ simulated formation pressure, the bottle testing method was more prone to evaporation. In addition, the bottle test and any analogous bulk test does not mimic an in situ gelation process that would occur as the gel solution flows in a formation, not only due to non-representative pressures, but also due to a lack of continuous flow within the formation.

For the purposes of describing and defining the present method, it is noted that reference in this application to a characteristic of the subject matter of the present disclosure being a "function of" a parameter, variable, or other characteristic is not intended to denote that the characteristic is exclusively a function of the listed parameter, variable, or characteristic. Rather, reference in this application to a characteristic that is a "function" of a listed parameter, variable, etcetera, is intended to be open ended such that the characteristic may be a function of a single parameter, variable, etcetera, or a plurality of parameters, variables, etcetera.

It is also noted that recitations in this application of "at least one" component, element, etcetera, should not be used to create an inference that the alternative use of the articles "a" or "an" should be limited to a single component, element, etcetera.

For the purposes of describing and defining the present method it is noted that the term "approximately" is utilized in this application to represent the inherent degree of uncertainty that may be attributed to any quantitative comparison, value, measurement, or other representation. The term "approximately" is also utilized in this application to represent the degree by which a quantitative representation may vary from a stated reference without resulting in a change in the basic function of the subject matter at issue.

Having described the subject matter of the present disclosure in detail and by reference to specific embodiments, it is noted that the various details disclosed in this application should not be taken to imply that these details relate to elements that are essential components of the various embodiments described in this application, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified in this application as preferred or particularly advantageous, it is contemplated that the present disclosure is not necessarily limited to these aspects.

What is claimed is:

1. A method of determining gelation time comprising:
    placing a composite core plug into a core holder of a vessel, in which the composite core plug comprises a first core plug, and a second core plug and a third core plug disposed on opposite sides of the first core plug, in which the second and third core plugs are saturated with polymer solution, and the first core plug is saturated with gel solution comprising polymer and crosslinker;
    alternating polymer solution injections between a first injection area located on the second core plug and a second injection area located on the third core plug, while ensuring that the polymer solution is being continuously fed via the injections to the composite core plug; and
    monitoring a pressure drop across the composite core plug during the alternating injection of polymer solution to determine the gelation time of the gel solution in the first core plug.

2. The method of claim 1, in which the ensuring that the polymer solution is being continuously fed to the composite core plug results in maintaining polymer concentration within the gel solution and ensuring that the gel solution is continuously flowing within the first core plug.

3. The method of claim 1, in which the alternating polymer solution injections and monitoring the pressure drop of the composite core plug are conducted with a backpressure from 50 to 350 psi.

4. The method of claim 1, in which the alternating polymer solution injections and monitoring the pressure drop across the composite core plug are conducted at a temperature from 50 to 150° C.

5. The method of claim 1, in which the method further comprises saturating the second, and third core plugs with an aqueous solution.

6. The method of claim 5, in which the method further comprises saturating the first core plug with the gel solution and displacing an aqueous solution.

7. The method of claim 5, in which the method further comprises saturating the second and third core plugs with the polymer solution and displacing the aqueous solution.

8. The method of claim 1, in which the alternating polymer solution injections and monitoring the pressure drop across the composite core plug are conducted at a confining pressure from 300 to 2500 psi.

9. The method of claim 1, in which the polymer solution comprises at least one of polyacrylamide, acrylamide copolymers, biopolymers, polysaccharides, and xanthan gum.

10. The method of claim 1, in which the crosslinker comprises at least one of hexamethylenetetramine, resorcinol, chromium acetate, chromium malonate, and polyethyleneimine.

11. The method of claim 1, in which the polymer solution comprises a viscosity within 5% of a viscosity of the gel solution.

12. The method of claim 1, in which the polymer solution comprises a weight averaged molecular weight from 10 million to 30 million Daltons.

13. The method of claim 1, in which the polymer solution comprises a hydrolysis degree from 20% to 40%.

14. The method of claim 1, in which the alternating polymer solution injections further comprises injecting up to 0.5 pore volume of the first core plug per injection.

15. The method of claim 1, in which the alternating polymer solution injections further comprises:
    injecting up to 1 pore volume of the second core plug per injection into the third core plug; and
    injecting up to 1 pore volume of the third core plug per injection into the second core plug.

16. The method of claim 1, in which:
    the alternating polymer solution injections further comprises injecting up to 0.2 pore volume of the first core plug per injection; and
    the polymer solution comprises an aqueous solution.

17. The method of claim 1, in which the alternating polymer solution injections further comprises injecting equal amounts of polymer solution in each injection.

18. The method of claim 1, in which the alternating polymer solution injections further comprises injecting the polymer solution at a constant flow rate.

19. The method of claim 18, in which the constant flow rate is from 0.05 to 0.2 ml/m.

20. The method of claim 1, in which the second core plug comprises a diameter, porosity, and permeability within 0.1% of a diameter, porosity, and permeability of the third core plug.

* * * * *